(12) United States Patent
Anchieta Da Silva et al.

(10) Patent No.: US 11,382,547 B2
(45) Date of Patent: Jul. 12, 2022

(54) BRAIN STIMULATION SYSTEM TO PROVIDE A SENSE OF WELLBEING

(71) Applicant: EMBRAER S.A., São José dos Campos CEP—SP (BR)

(72) Inventors: Paulo Anchieta Da Silva, São José dos Campos CEP—SP (BR); Flavia Renata Dantas Alves Silva Ciaccia, São José dos Campos CEP—SP (BR)

(73) Assignee: Embraer S.A., Sâo José dos Campos-SP (BR)

( * ) Notice: Subject to any disclaimer, the term of this patent is extended or adjusted under 35 U.S.C. 154(b) by 195 days.

(21) Appl. No.: 16/332,173

(22) PCT Filed: Sep. 12, 2016

(86) PCT No.: PCT/BR2016/000090
§ 371 (c)(1),
(2) Date: Mar. 11, 2019

(87) PCT Pub. No.: WO2018/045438
PCT Pub. Date: Mar. 15, 2018

(65) Prior Publication Data
US 2019/0231243 A1 Aug. 1, 2019

(51) Int. Cl.
*G16H 20/00* (2018.01)
*A61B 5/16* (2006.01)
(Continued)

(52) U.S. Cl.
CPC ............ *A61B 5/165* (2013.01); *A61B 5/4836* (2013.01); *G16H 50/20* (2018.01); *A61B 5/0077* (2013.01);
(Continued)

(58) Field of Classification Search
CPC ....... A61B 5/024; A61B 5/165; A61B 5/4836; A61B 5/077; G02B 27/017; G16H 20/00; G16H 50/20; G16H 50/30
See application file for complete search history.

(56) References Cited

U.S. PATENT DOCUMENTS

2009/0306741 A1 12/2009 Hogle et al.
2010/0134302 A1 6/2010 Ahn et al.
(Continued)

FOREIGN PATENT DOCUMENTS

WO 2013192582 A1 12/2013

OTHER PUBLICATIONS

International Search Report for PCT/BR2016/000090 dated May 19, 2017, 5 pages.
(Continued)

*Primary Examiner* — Michael J D'Abreu
(74) *Attorney, Agent, or Firm* — Nixon & Vanderhye P.C.

(57) ABSTRACT

A system and method provides noninvasive mental state diagnostics and brain stimulation via consensual transcranial stimulation. The method utilizes face recognition associated with known physiologic measures to identify an emotional state-of-mind of a human subject and then provides or at least suggests a transcranial stimulation treatment for enhancing mental focus or for alleviating discomfort or anxiety by inducing a feeling of well-being. An example system arrangement utilizes a camera to scan a subject's facial expressions and, if the subject desires, provides a transcranial stimulation to the subject based upon an analysis of the facial expression. In one example environment, the system is used in the office or other workplace. In another example environment, the system is used in conjunction with a vehicle seat, such as for example a seat in a car, train, aircraft or other vehicle. All or parts of the system may be
(Continued)

incorporated within or near a seat and includes at least a camera for obtaining images of the subject's face, body sensors that measure physiologic characteristics, a user interface device which may include a display and touch controls for input, and a hardware processor for analyzing the scan of the subject's facial expression and operating the user interface device.

21 Claims, 3 Drawing Sheets

(51) Int. Cl.
    *A61B 5/00*         (2006.01)
    *G16H 50/20*       (2018.01)
    *G16H 30/20*       (2018.01)
    *A61M 21/02*       (2006.01)
    *G16H 50/30*       (2018.01)

(52) U.S. Cl.
    CPC ............ *A61M 21/02* (2013.01); *G16H 30/20* (2018.01); *G16H 50/30* (2018.01)

(56) References Cited

U.S. PATENT DOCUMENTS

| | | | |
|---|---|---|---|
| 2012/0283502 | A1 | 11/2012 | Mishelevich et al. |
| 2014/0330350 | A1 | 11/2014 | Kokos |
| 2015/0174418 | A1 | 6/2015 | Tyler et al. |
| 2016/0220163 | A1 | 8/2016 | Yamada et al. |
| 2016/0256691 | A1 | 9/2016 | Cecchi et al. |
| 2017/0291037 | A1* | 10/2017 | Tamiya .................... A61N 2/02 |
| 2017/0323485 | A1* | 11/2017 | Samec ..................... A61B 7/04 |

OTHER PUBLICATIONS

Written Opinion of the ISA for PCT/BR2016/000090 dated May 19, 2017, 7 pages.
"Transcranial direct-current stimulation", Wikipedia, last edited on Jan. 15, 2021, https://en.wikipedia.org/wiki/Transcranial_direct-current_stimulation (14 pages).
Brunoni et al., "Transcranial Direct Current Stimulation in Neuropsychiatric Disorders: Clinical Principles and Management", pp. 293-298 (Springer 2016) (7 pages).
"Transcranial magnetic stimulation", Wikipedia, lasted edited on Jan. 20, 2021, https://en.wikipedia.org/wiki/Transcranial_magnetic_stimulation (17 pages).
Nitsche et al., "Transcranial direct current stimulation: State of the art 2008", pp. 203-223, vol. 1, No. 3 (Brain Stimulation 2008) (18 pages).
Thync, Neurostimulation For Everyone (Thync Global, Inc., 2021), www.thync.com (6 pages).
"Transcranial pulsed ultrasound", Wikipedia, last edited on Dec. 22, 2020, https://en.wikipedia.org/wiki/Transcranial_pulsed_ultrasound (3 pages).
Black et al., "Recognizing Facial Expressions in Image Sequences Using Local Parameterized Models of Image Motion", pp. 23-48, No. 25, No. 1 (International Journal of Computer Vision 1997) (26 pages).
Cohn et al., "Feature-Point Tracking by Optical Flow Discriminates Subtle Differences in Facial Expression", pp. 396-401 (Proc. Jnt'l Conf. Automatic Face and Gesture Recognition 1998) (6 pages).
Schut et al., "Biometrics for Emotion Detection (BED1): Exploring the combination of Speech and ECG", Workshop an Bio-inspired Human-machine interfaces and healthcare applications—B interfaces (Spain. 2010) (8 pages).
Monajati et al., "Emotions States Recognition Based on Physiological Parameters by Employing of Fuzzy-Adaptive Resonance Theory", pp. 166-175, vol. 2 (International Journal of Intelligence Science, 2012) (12 pages).
Sharma et al., "Emotion estimation of physiological signals by using low power embedded system", Conference on Advances in Communication and Control Systems 2013 (CAC2S 2013) (4 pages).
Fitzgerald et al, Repetitive Transcranial Stimulation Treatment For Depressive Disorders: A Practical Guide (Springer 2013) (textbook; no copy submitted).
Holtzheimer et al, A Clinical Guide to Transcranial Magnetic Stimulation (Oxford University Press 2014) (textbook; no copy submitted).
Reti, Brain Stimulation: Methodologies and Interventions (Wiley-Blackwell 2015) (textbook; no copy submitted).
M. Pantic et al, Expert System for Automatic Analysis of Facial Expressions, vol. 18, No. 11, pp. 881-905, (Image and Vision Computing 2000) (abstract).
Edwards et al, "Face Recognition Using Active Appearance Model", vol. 2, pp. 581-695 (Proc. European Conference on Computer Vision 1998) (abstract).
G.J. Edwards, T.F. Cootes, C.J. Taylor, "Active Appearance Models", vol. 2, pp. 484-498 (Proc. European Conf. Computer Vision 1998) (abstract).
Application Note 276: "Emotional State Recognition via Physiological Measurement and processing.", www.biopac.com (2014) (abstract).
Mikuckas et al, "Emotion Recognition in Human Computer interaction systems", vol. 20, No. 10, Elektronika Ir Elektrotechnika, ISSN 1392-1215 (2014) (abstract).
Pantic et al, "Automatic Analysis of Facial Expressions: The State of the Art", IEEE Transactions on Pattern Analysis and Machine Intelligence, vol. 22, No. 12 (Dec. 2000).

\* cited by examiner

BRAIN STIMULATION SYSTEM TO PROVIDE A SENSE OF WELLBEING

CROSS-REFERENCE TO RELATED APPLICATIONS

This application is the U.S. national phase of International Application No. PCT/BR2016/000090 filed Sep. 12, 2016 which designated the U.S., the entire contents of which are hereby incorporated by reference.

STATEMENT REGARDING FEDERALLY SPONSORED RESEARCH OR DEVELOPMENT

None.

FIELD

The technology herein relates generally to noninvasive systems and methods for diagnostic and intervention that utilize face recognition associated with other physiologic measures to identify the emotions and state-of-mind of a human subject and to suggest a treatment against discomfort or anxiety, which may enhance mental focus or induce a feeling of well-being. More particularly, the technology herein relates to an environment and system for providing a consensual transcranial stimulation to a subject and an associated user interface, as well as providing enhanced physical and mental performance, such as relaxation and concentration, to perform daily activities.

BACKGROUND AND SUMMARY

Nowadays, society is anxious and impatient. People are always in a hurry, running from place to place and always being late for appointments. As never before, people use antidepressants and have sleeping problems. On the other hand, there are more and more people concerned about health and wellbeing, searching for alternatives to lower stress and anxiety such as, for example, music applications which may promote concentration and focus.

For example, people can experience substantial anxiety and stress in the work environment. Instead of focusing on their work, people may be distracted by sadness, depression or other emotional states. Employees suffering from high stress-induced emotional states tend to have lower engagement, are less productive and have higher absenteeism levels than those not working under too much pressure. Employers and employees alike have an interest in maintaining focus and productivity in the workplace.

Some people become anxious when riding in a vehicle such as a car, a train or an airplane. Anxiety can be unpleasant, turning a short trip into a long one. It is very humane to relieve another subject's fear and anxiety. Mammals are very skilled at ascertaining and affecting the emotional stage of other mammals, but so far in the past, machines have been much less effective.

However, with the advent of brain stimulation, neurological diseases such as major depression have been effectively treated. The successful development of new interventions for neurological diseases of the brain using cranial stimulation technologies additionally have brought the opportunity to improve cognitive performance and reduce stress.

The brain continuously receives and translates sensory information from multiple sensory sources including, for example, visual auditory, olfactory, and tactile sources. Through processing, movement, and awareness training, subjects have been able to recover and enhance sensory perception, discrimination, and memory, demonstrating a range of untapped capabilities.

Stimulation technologies that affect electric fields and electrochemical signaling in neurons can modulate the pattern of neural activity and cause altered behavior, cognitive states, perception, motor output, and more.

Some devices combine brain and audiovisual stimulation, whereby the brain is stimulated by sound signals entering the ears and/or by visual stimulation using eye glasses with LED diodes or patterns on a screen in front of the eyes of a treated subject. The brain can also be stimulated using sources of magnetic fields near or in contact with the scalp of the head, while fields are changed according to a program that controls their alteration. Devices producing visual stimulation using bright flashing lights along with adjusted sound frequencies provided to subject's ear are also known. All such devices primarily focus on providing stimulation to the brain by using frequencies from external sources.

Although such prior methods and apparatus have been proposed to treat neurological diseases or to improve comfort, relaxation and awareness, these prior systems, methods and apparatus do not provide any diagnostic of the emotional state-of-mind of an individual and do not provide or suggest any treatment for it. For example, at least one transcranial electrical stimulation requires extensive input data concerning the subject in order to function.

Ideally, such systems and methods should improve the convenience of usage and should employ effective strategies for diagnosing the emotional state-of-mind of the subject as well as provide treatments to improve cognitive performance, enhance mental focus attention and/or promote a feeling of well-being and relaxation. Also, there is a need for systems and methods which could be combined with other noninvasive physiological measurements so as to better recognize the particular state-of-mind of a subject.

BRIEF DESCRIPTION OF THE DRAWINGS

The following detailed description of exemplary non-limiting illustrative embodiments is to be read in conjunction with the drawings of which.

DETAILED DESCRIPTION OF PREFERRED EMBODIMENTS

The example non-limiting technology herein minimizes or eliminates inconvenience by providing a mechanism and environment for real-time monitoring the emotions and state-of-mind of a human and providing treatments for improving cognitive performance and feeling of well-being via in situ brain stimulation.

The non-limiting example embodiments disclosed herein generally relate to a system and method for noninvasive intervention and diagnostics that uses face recognition associated with other physiologic measures to identify a state of mind of a subject, as well as to provide a possible suggested treatment to alleviate that subject's discomfort or anxiety. An integrated system of hardware processing, memory, user interfacing and stimulation devices, camera and/or other body sensors are used to provide a consensual transcranial stimulation to a subject in a manner capable of quickly producing an enhanced physical feeling or improved mental performance (for example, but not limited to, enhanced relaxation and concentration).

For example, a digital camera is used to record and register the complex movements of a subject's face and through the use of conventional mathematical analysis and pattern matching the images are evaluated to obtain a diagnostic indicative of an emotional status of the subject, such as, the following non-limiting examples:

Happy
Confused
Sad
Smiling
Attentive
Depressed
Anxious
Dejected
Afraid
Angry
Other.

In one non-limiting exemplary implementation, a system of components is provided that is capable of capturing and recording images of a human subject seated in a vehicle and includes a camera, body sensors and a hardware processor (e.g., a programmable computer) that utilizes one or more conventional mathematician algorithms to analyze the emotional state of the seated subject from the captured images. The resulting analysis may be used to initiate operations by other hardware components for providing a transcranial stimulation to the subject to enhance that subject's mental performance and physical well-being. The components of the system may be independently exchanging information as needed or integrated into a single device.

Accordingly, the technology described herein may be embodied as a method, a system, as embedded firmware in a hardware processor or conventional computer, as a whole integrated product or as a set of individual components that work together.

Figure 1:
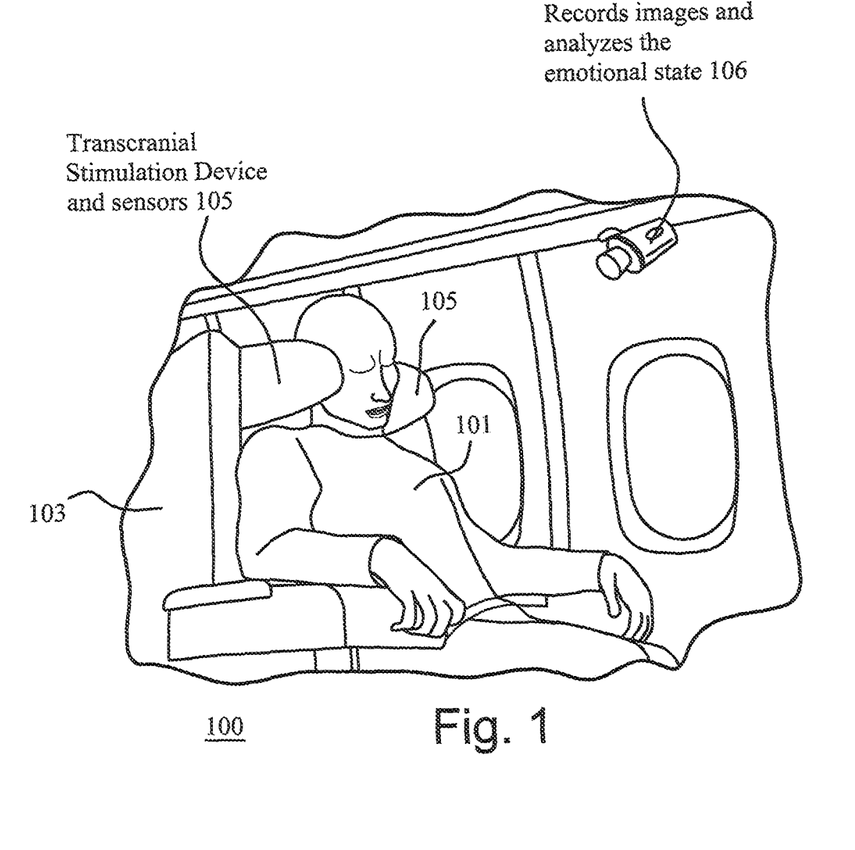
FIG. 1 shows non-limiting example components and an environment in which the presently disclosed system and method may be used.

FIG. 1 illustrates a non-limiting example environment 100 within a vehicle such as an airplane and a system for obtaining a diagnostic of a seated subject's emotional state-of-mind. The system provides the subject with an appropriate stimulation to the brain to, for example, help alleviate detected anxiety and/or promote an improved mental focus or create a feeling of well-being. In this example vehicle environment 100, subject 101 is provided a seat 103 that is outfitted with a transcranial stimulation inducing device that is incorporated into seat head-rest 105. A camera 106, or other image capturing device is mounted in the vehicle environment nearby the subject 101 at a position and orientation to capture images of at least the face of subject 101. Other types of physiological or biological sensors may also be incorporated into seat 103 or head-rest 105 to acquire or monitor other types of physiological conditions and obtain information pertaining to the mental or physical state of subject 101. For example, physiological measurements can be taken from body sensors placed in different parts of a seat such as a back rest, neck rest, head rest, seat pan, etc.

At least one non-limiting example method employing the system of FIG. 1 for providing a subject a sense of well-being or enhanced mental focus comprises steps of:
  using a camera for scanning a subject's facial expression using a body/biological sensor(s) to acquire physiological measurements;
  developing a diagnostic analysis of the emotional state of the subject from one or more images of the subject's facial expressions obtained from the camera and from the body/biological sensors;
  using the results of the analysis of emotional state and consensual process;
  using the diagnostic analysis to determine an appropriate brain stimulation; and
  providing a consensual transcranial stimulation to the subject via a seat-mounted device located at or near the head of the subject.

Figure 2:
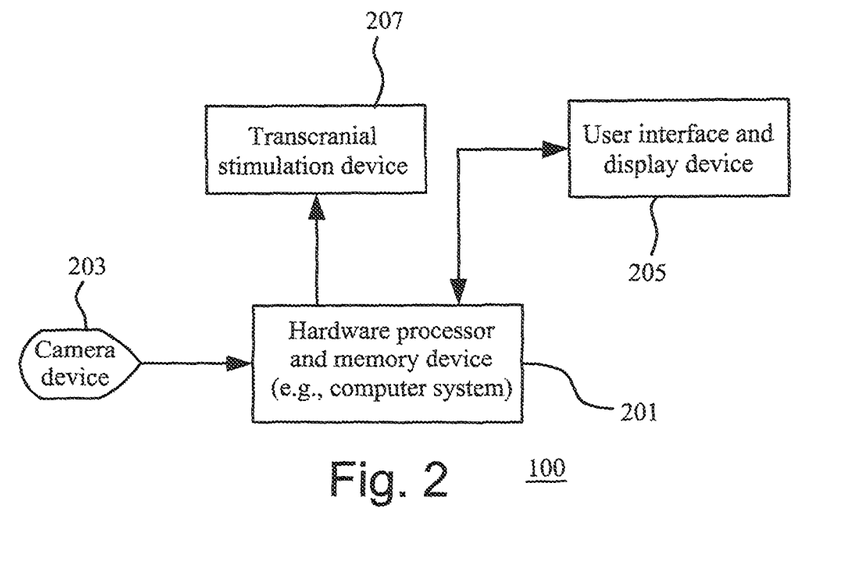
FIG. 2 shows non-limiting example hardware components and arrangement for implementing a non-invasive diagnostic and consensual transcranial stimulation system.

FIG. 2 illustrates a non-limiting example hardware system 200 and arrangement of functional components which may be used to implement a diagnostic of a subject's emotional state and provide an appropriate stimulation to the subject in response to the diagnostic. In the example arrangement shown in FIG. 2, system 200 includes a hardware processor device 201, which may include a computer processor having appropriate data/program storage capabilities in the form of digital memory devices. Alternatively, in appropriate environments, system 200 may utilize a remote server computer system and communicate with such wirelessly or hardware processor 201 may be a connected local mobile computing device such as a laptop, handheld computer or the like. The processor system device 201 accepts input image data from a camera device 203 or other image sensor or sensors, and from body/biological sensor or sensors 209 and stores or records the acquired data (which may include image data in one non-limiting embodiment) in memory. The processor system/device 201 may utilize an appropriate software or firmware algorithm to analyze the acquired images to develop diagnostic information that analyzes the emotional state of the subject. The system 200 may also include a user interface 205 which may include, other input sensors for obtaining information about a subject and/or one or more other input/output devices such as a display and keypad for communicating with a subject. While a seat-based embedded implementation is generally preferred, in some non-limiting implementations, the processor system device 201 may comprise a smart phone or other handheld or portable device that communicates wirelessly or by wires with one or more transcranial stimulation device(s) 207 to be described below.

In addition, system 200 includes a transcranial stimulation device 207 that receives appropriate output control signals from processor device 200 which enable it to provide/produce a brain stimulation effect to the subject. Exemplary transcranial stimulation techniques which are contemplated for use with an appropriate transcranial stimulation device 207 may include, but are not limited to, direct current transcranial stimulation (tDCS) devices, repetitive transcranial magnetic stimulation (rTMS) devices and transcranial pulsed ultrasound (TPU) devices, among others. Further details regarding the mechanism of action and operation of each may be found, for example, from various reference materials including the following each of which is incorporated herein by reference:
  https://en.wikipedia.org/wiki/Transcranial_direct-current_stimulation, Brunoni et al, Transcranial Direct Current Stimulation in Neuropsychiatric Disorders: Clinical Principles and Management (Springer 2016);

https://en.wikipedia.org/wiki/Transcranial_magnetic_stimulation,

Fitzgerald et al, Repetitive Transcranial Stimulation Treatment For Depressive Disorders: A Practical Guide (Springer 2013);

Holtzheimer et al, A Clinical Guide to Transcranial Magnetic Stimulation (Oxford University Press 2014); Nitsche et al, "Transcranial direct current stimulation: State of the art 2008", Brain Stimulation Volume 1, Issue 3, Pages 206-223 (July 2008); www.thync.com; https://en.wikipedia.org/wiki/Transcranial_pulsed_ultrasound.

Reti, Brain Stimulation: Methodologies and Interventions (Wiley-Blackwell 2015).

For example, transcranial direct current stimulation (tDCS) is a form of neurostimulation which uses constant, low current delivered to the brain area of interest via electrodes on the scalp. Transcranial direct current stimulation works by sending constant, low direct current through the electrodes. Hence, transcranial direct current stimulation (tDCS), is a non-invasive, painless brain stimulation treatment that uses direct electrical currents to stimulate specific parts of the brain. A constant, low intensity current is passed through two electrodes placed over the head which modulates neuronal activity. There are two types of stimulation with tDCS: anodal and cathodal stimulation. Anodal stimulation acts to excite neuronal activity while cathodal stimulation inhibits or reduces neuronal activity. Although tDCS is still an experimental form of brain stimulation, it potentially has several advantages over other brain stimulation techniques. It is cheap, non-invasive, painless and safe. It is also easy to administer and the equipment is easily portable. The most common side effect of tDCS is a slight itching or tingling on the scalp.

In one non-limiting embodiment, electrodes are placed in the region of interest, the current induces intracerebral current flow. This current flow then either increases or decreases the neuronal excitability in the specific area being stimulated based on which type of stimulation is being used. This change of neuronal excitability leads to alteration of brain function, which can be used in various therapies as well as to provide more information about the functioning of the human brain. Transcranial direct current stimulation is a relatively simple technique requiring only a few parts. These include a tDCS device having at least two electrodes and a power source that delivers constant current via the electrodes. The tDCS device has at least one anodal, positively charged electrode and a cathodal, negative electrode. A tDCS device controller, such as for example controller 200, may include appropriate control software used to control the tDCS device to provide differing stimulation types. Preferably, the electrodes are packaged in a way that provides ease of use and good connectivity. For example, they may be provided with adhesives that allow the electrodes to be stuck to the subject's head in specified locations in order to render efficacious therapy.

In biological systems, such as the human head, a current is usually created by the flow of ions, which may be positively or negatively charged—positive ions will flow towards the cathode; negative ions will flow toward the anode. The tDCS device controller may control the current as well as the duration of stimulation. In the example system shown in FIGS. 1 and 2, the electrodes could be applied by the subject or to the subject by an attendant and would be connected to and controlled by, for example, hardware processor 200.

Figure 3A:
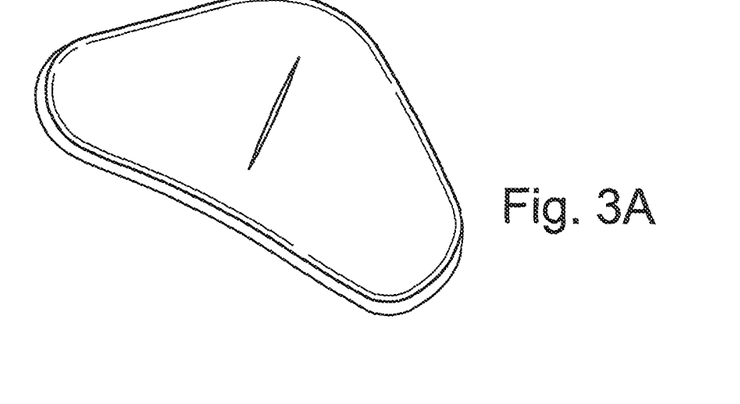
FIGS. 3A, 3B, 3C show non-limiting prior art example electrodes which may be used to provide transcranial direct current stimulation (tDCS) using the system and apparatus of FIGS. 1 and 2.
Figure 3B:
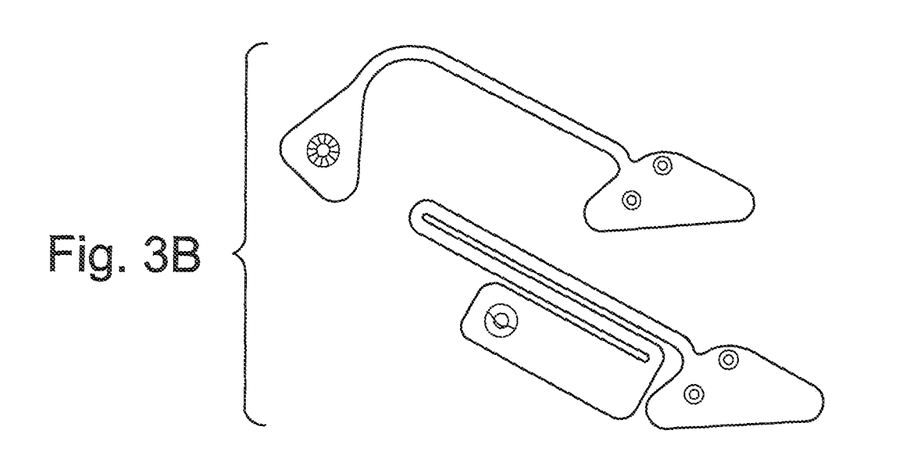
Figure 3C:
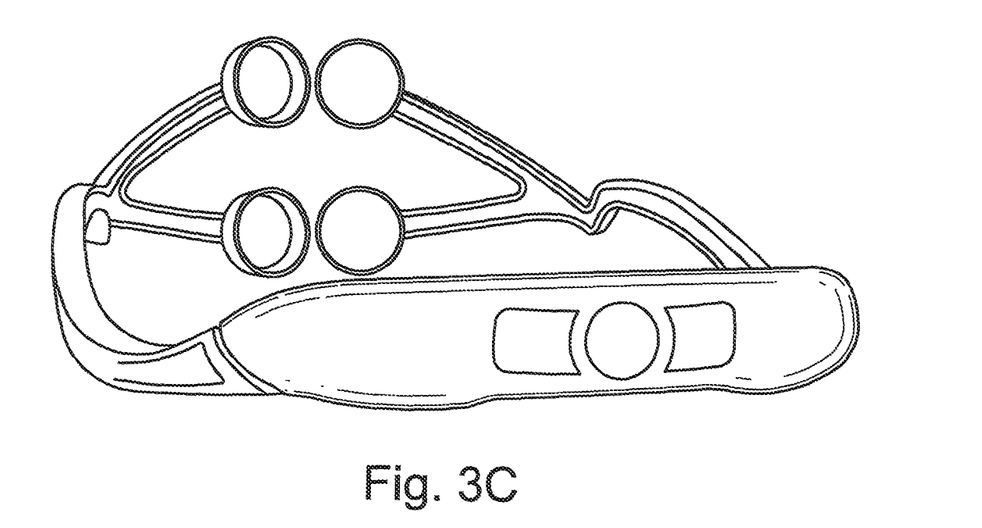

FIGS. 3A, 3B and 3C illustrate some non-limiting prior art commercial example tDCS forehead module and electrode devices which may be applied to the forehead and neck, FIG. 3A illustrates a forehead electrode module. FIG. 3B illustrates neck electrodes. FIG. 3C illustrates another non-limiting example wearable headset tDCS device having four electrode pads and a forehead module which deliver an intracranial stimulation. Such equipment is available from a number of different manufacturers and suppliers and has the advantage of being rugged and reusable.

Another example technique utilizes repetitive transcranial magnetic stimulation (rTMS). Transcranial magnetic stimulation (TMS) is a magnetic method used to stimulate specific regions of the brain. TMS is a non-invasive method of brain stimulation that relies on electromagnetic induction using an insulated coil placed over the scalp, focused on an area of the brain thought to play a role in mood regulation. The coil generates brief magnetic pulses, which pass easily and painlessly through the skull and into the brain. The pulses generated are of the same type and strength as those generated by magnetic resonance imaging (MRI) machines. When these pulses are administered in rapid succession, it is referred to as "repetitive TMS" or "rTMS", which can produce longer lasting changes in brain activity. rTMS has been shown to be a safe and well-tolerated procedure that can be an effective treatment for patients with depression.

During a repetitive TMS procedure, a magnetic field generator, or "coil", is placed near the head of the subject receiving the treatment and repetitive pulsed currents are applied to the coil. The coil produces small electric currents in the region of the brain just under the coil via electromagnetic induction. Conventionally, the coil is connected to a pulse generator, or other stimulator, that delivers pulsed electric current to the coil. In the example system shown in FIGS. 1 and 2, the coil and pulse generator could be integrated within seat 103 and headrest 105 and would be connected to and controlled by, for example, hardware processor 200. The hardware processor 200 may control the intensity, duration, pulse pattern, and other characteristics of the magnetic pulses e.g., in response to sensed signals provided by the camera and/or the body sensors.

Another example technique utilizes transcranial pulsed ultrasound (TPU) which employs low intensity, low frequency ultrasound (LILFU) as a method to stimulate the brain. The low-power ultrasound is able to stimulate high neuron activity which allows for the manipulation of the brain waves through an external source such as ultrasonic transducers. TPU is a noninvasive procedure that does not require the use or implantation of electrodes. In the example system shown in FIGS. 1 and 2, low frequency ultrasound emitters or transducers could be integrated within seat 103 and headrest 105 and would be connected to and controlled by, for example, hardware processor 200.

It is contemplated that for the exemplary use environment of FIG. 1, the intracranial brain stimulation is administered only upon first obtaining consensus from the subject. The intracranial stimulation provided by the system in this non-limiting example process of FIG. 4 utilizes a camera device to obtain video images of a subject's facial expression and/or utilizes information from sensors of other monitored physiological parameters of the subject and uses known analysis techniques employing processor system 201 to determine an emotional state of the subject. Some example known analysis techniques for determining emotional state from facial images and other physiological parameters are provided in the following articles/publications, which are hereby incorporated herein by reference:

- M. Pantic, L. Rothkrantz, "Automatic Analysis of Facial Expressions: The State of the Art", IEEE Transactions on Pattern Analysis and Machine Intelligence, Vol. 22, No. 12, December 2000;
- M. Pantic, L. Rothkrantz, Expert System for Automatic Analysis of Facial Expressions, Image and Vision Computing, Vol. 18, No. 11, pp. 881-905, 2000;
- M. J. Black, Y. Yacoob, "Recognizing Facial Expressions in Image Sequences Using Local Parameterized Models of image Motion", Int'l J. Computer Vision, Vol. 25, no.1, pp. 23-48, 1997;
- J. F. Cohn, A. J. Zlochower, J. J. Lien, T. Kanade, "Feature-Point Tracking by Optical Flow Discriminates Subtle Differences in Facial Expression", Proc. Int'l Conf. Automatic Face and Gesture Recognition, pp. 396-401, 1998;
- G. J. Edwards, T. F. Cootes, C. J. Taylor, "Face Recognition Using Active Appearance Models", Proc. European Conference on Computer Vision, Vol. 2, pp. 582-695, 1998;
- G. J. Edwards, T. F. Cootes, C. J. Taylor, "Active Appearance Models", Proc. European Conf. Computer Vision, Vol. 2, pp. 484-498, 1998;
- Marleen H. Schut1, Kees Tuinenbreijer1, Egon L. van den Broek2, and Joyce H. D. M. Westerink3 Biometrics for Emotion Detection (BED1): Exploring the combination of Speech and ECG. Workshop on Bio-inspired Human-machine interfaces and healthcare applications—B interfaces. Spain. 2010;
- Application Note 276: "Emotional State Recognition via Physiological Measurement and processing.", www.boipac.com, 2014;
- A. Mikuckas, I. Mikuckiene, A. Venckauskas, E. Kazanavicius, R. Lukas, I. Plauska Emotion Recognition in Human Computer Interaction systems, ELEKTRONIKA IR ELEKTROTECHNIKA, ISSN 1392-1215, VOL. 20, NO. 10, 2014;
- Mandis Monajati, Seyed Hamidreza Abbasi, Fereidoon Shabaninia, Sina Shamekhi. Emotions States Recognition Based on Physiological parameters by Employing of Fuzzy-Adaptive Resonance Theory. International Journal of Intelligence Science, 2012, 2, 166-175;
- Tanu Sharma; Bhanu Kapoor. Emotion estimation of physiological signals by using low power embedded system. Conference on Advances in Communication and Control Systems 2013 (CAC2S 2013).

The analysis performed by processor system 201 is used to select the appropriate type, mode or operation of intracranial stimulation to result in inducing a change in the mental state of the subject to bring about a feeling of well-being or a feeling of improved mental focus for such purposes as, for example, to assist the subject in relaxing, reading or focusing their attention for specific mental tasks. Such selection can extend to selecting between modes of stimulation (e.g., duration, frequency, repetition rate, waveform, etc.) and/or different types of stimulating (e.g., direct electrode stimulation, magnetic, etc.)

Figure 4:
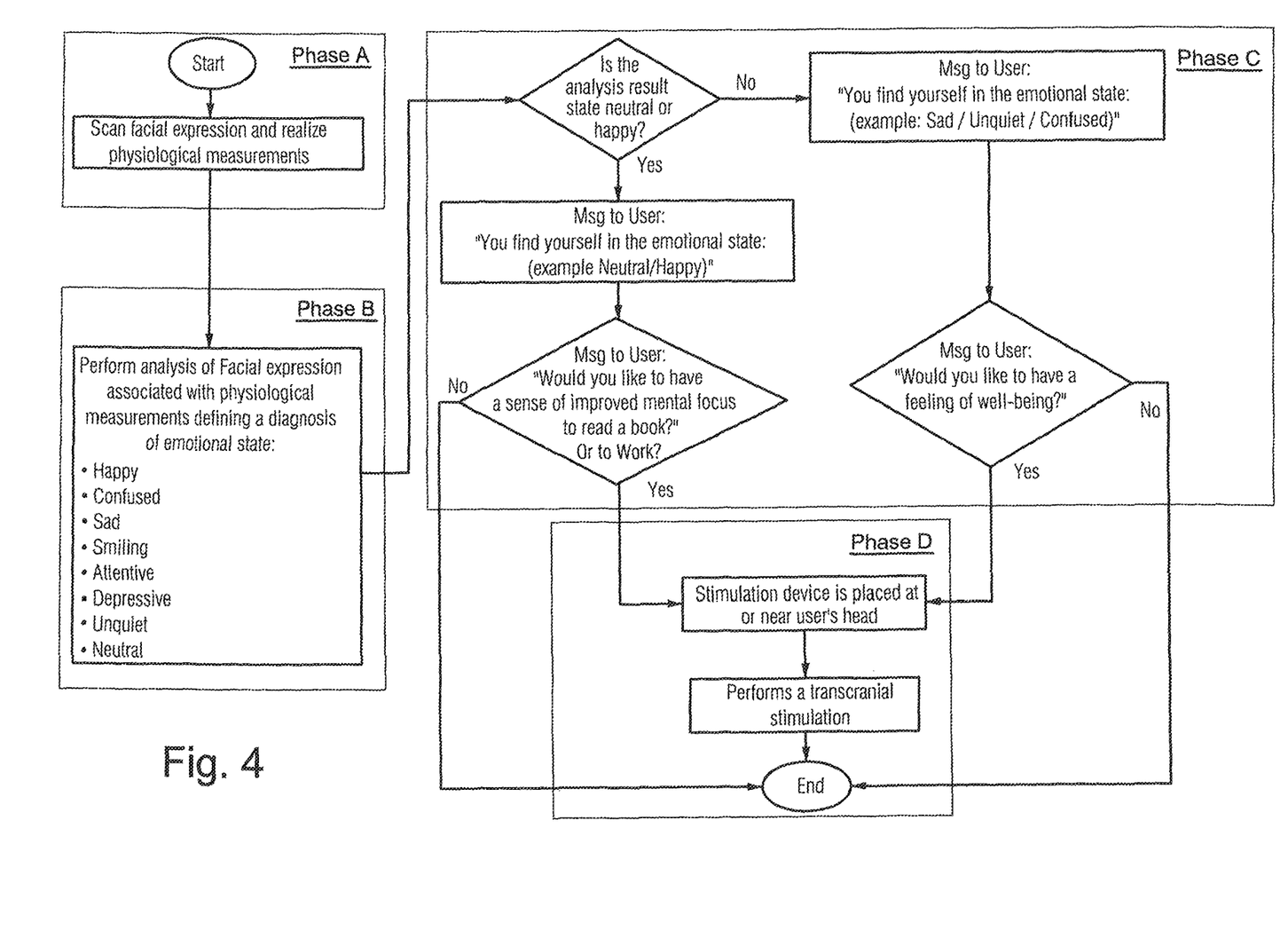
FIG. 4 shows a non-limiting example process flow chart implemented by a hardware processor for performing a non-invasive diagnostic and consensual transcranial stimulation of a subject.

Referring to FIG. 4, a non-limiting example flow chart depicts an example of a method used in a vehicle for evaluating the emotional state of a subject and for providing an intracranial stimulation. The intracranial stimulation is administered to the subject only upon obtain consent from the subject, and results in inducing a change in the mental state of the subject to bring about a feeling of well-being or improved mental focus, for example, to assist the subject in relaxing, reading or focusing their attention for other mental tasks.

The flowchart of FIG. 4 is segmented into four consecutive operational phases A-D to better illustrate an example process performed by hardware processor 201:

Phase A—Scanning of Facial Expressions to Realize Physiological Measurements

In phase A of the example process, a camera 106 is installed near to an office or passenger seat and which is capable of acquiring images of the facial expressions (including microexpressions) of the subject and recording these images or providing the images to processor system 201. For example, a video monitor 106 may be installed in front of a seat 103 to enable real-time capture of images of the seated subject.

Also it is contemplated that physiological measuring devices 104 are installed near to the seat 103 which are capable of measuring the physiological information of the subject such as for example, but not limited to, body temperature, respiratory rate, heart rate, pulse oximetry, body posture, etc.

It is also contemplated that an application server or other computer processor system having facial expression analysis software and which is capable of storing acquired image signals from the camera or from any physiological measuring devices or sensors that may be used.

It is contemplated that software installed in the processor system 201 or application server (herein called "User's interface SW"), will execute user interface 205 commands providing a touch display of the video monitor or other input device for the subject to interact with the system.

Accordingly, the subject may voluntarily start the process for scanning or capturing an image of his/her face and for capturing other physiological measurements. The signals are then acquired by the digital camera and biological sensors and sent to the video monitor as well as being digitized and stored in the application server.

If after starting, the processor system 201 cannot obtain identification and recognition of a human face or signal from biological sensors then. User's Interface SW will send a real-time image the seat 103 which will appear in the user interface display device 205 with no additional message for indicating a diagnostic of the emotional status.

If processor system 201 obtains an identification and recognition of a human face and signals from biological sensors then, User's interface SW will send a real-time image of the subject and provide a display of the image along with a message such as; "Please Wait. The system is performing a diagnostic of your emotional State," and then will start the process of Phase B: Diagnostic of the Emotional. State.

Phase B—Diagnostic of the Emotional State

In Phase B of the exemplary process, it is assumed that software/firmware program instructions (herein called "Diagnostic SW") are installed in the memory of processor system 201 which will execute the program and perform an analysis of captured images of the complex movements (including microexpressions) of the subject's face and evaluate any other sensor obtained physiological information to produce a diagnostic of the subject's emotional state.

In the example FIG. 1 vehicle environment, an interface command or input may be provided in the video monitor device for the seated subject or a personal device with the application compatible with the system 200 to approve a starting up of system operations.

User's interface SW starts the Diagnostic SW for an analysis of facial expression associated with physiological measurements defining a diagnosis of emotional state.

Diagnostic SW promotes the execution of several algorithms to perform a mathematical analysis. These algorithms perform a diagnosis of emotional state and the results are sent to and stored by processor system 201 or a remote application server.

Some example types of emotional states which may be indicated as a result of the analysis may include by way of non-limiting example:

Happy
Confused
Sad
Smiling
Attentive
Depressive
Unquiet
Upset
Angry
Anxious
Afraid
Neutral Phase C—Results of the Analysis of Emotional State and Consensual Process After obtaining an analysis result, the Users interface SW performs classification in order to fit the result into one of the groups described below:

Group 1: example Happy or Neutral
Group 2: example Confused/Sad/Smiling/Attentive/Depressive/Unquiet If the resulting analysis is in Group 1, User's interface SW sends a real-time image of the subject to display 205 with a message indicating: "You find yourself in the emotional state: (example: Neutral/Happy)".

User's interface SW sends a real-time image of the subject to display 205 with a message indicating: "Would you like to have brain stimulation to enhance your physical and mental performance: (example: such as improving concentration focus or to read a book? Or to perform other mental work?)".

If the result analysis is in Group 2: User's interface SW sends a real-time image of the subject to display 205 with a message indicating: "You find yourself in the following emotional state: (example: Confused/Sad/Smiling/Attentive/Depressive/Unquiet)".

User's interface SW may also send a real-time image of the subject to display 205 along with a message indicating: "Would you like to have brain stimulation for producing enhanced physical and mental performance: (example: such as for relaxation or to have a feeling of well-being)?".

If both the questions are defined within Group 1 or Group 2: the consensual answer of the subject "Yes" or "No" will start or not start the Phase D processes.

Phase D—Transcranial Stimulation

In Phase D, it is assumed that a device (herein called "a transcranial stimulation device") is installed on or within to a seat near to the head of the subject and is capable of performing some type of transcranial stimulation to the seated subject that results in providing that subject with an enhanced physical sense of well-being and mental performance, such as relaxation or enhanced mental focus and concentration.

The provision of transcranial stimulation is consensual, so if the subject does not agree by responding via the user interface 205 then the process is terminated and the User's interface SW sends a real-time image of the subject to appear in the display device 205 with an additional message indicating: "Example: Operation completed".

If the subject does agree to receive a transcranial stimulation, then the User's interface SW sends a real-time image of the subject to appear in the display device 205 with a message indicating: "Please put/position the transcranial stimulation device near your head".

Once the transcranial stimulation device is positioned at or near the subject's head, the system performs transcranial stimulation following the orientations defined by the results of the Diagnostic SW.

Once the process is finalized, the User's interface SW sends a real-time image of the subject to the display device 205 with a message indicating: "Example: Operation completed, Please take off the brain device".

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A system for providing noninvasive mental state diagnostics and brain stimulation via transcranial stimulation of a human subject occupying a passenger seat of the type including a headrest, the system comprising:
    a digital camera for scanning and providing an image of the subject's facial expression while the subject occupies the passenger seat;
    a hardware processor configured to analyze a facial expression image obtained by the camera to identify an emotion of the subject;
    one or more physiological measuring devices comprising one or more transducers, sensors or actuators adapted to measure a physiological parameter of the subject while the subject occupies the passenger seat;
    a user interface device having a display and an input device for inputting a command or response provided by the subject occupying the passenger seat;
    a device adapted for incorporation into the passenger seat headrest comprising one or more transducers, sensors or actuators configured to perform transcranial stimulation of the subject including controlling the intensity, duration, pulse pattern, and/or other characteristics of the transcranial stimulation based on the identified emotion of the subject while the subject occupies the passenger seat;
    an application server capable of storing data; and
    a storage device storing program instructions for configuring the hardware processor to perform emotional status identification and operate the user interface device.

2. The system according to claim 1 wherein the transcranial stimulation is performed through a brain device following orientations defined by the results of diagnostic software providing enhanced physical and mental performance, already installed near to the seat.

3. The system according to claim 2 wherein the system requests the subject's consent through of the user interface to perform transcranial stimulation on the subject.

4. The system according to claim 2 wherein before transcranial stimulation of the brain is initiated a transcranial stimulation device is positioned within the headrest at or near the head of the subject.

5. The system according to claim 2 wherein before the transcranial stimulation the subject is asked for his consent to proceed with non-invasive intervention.

6. The system according to claim 1 wherein the diagnostic of the emotional state is performed using facial action and physiological information coding technologies that automatically determine an emotional indicator of the subject.

7. The system according to claim 6 wherein before performing the diagnostic of emotional state, diagnostic software is installed in the application server and is capable of executing the analyses of complex movements of a human face and evaluating obtained physiological information to perform a diagnostic of the emotional state.

8. The system according to claim 6 wherein before performing the diagnostic of the emotional state, diagnostic software promotes an execution of several algorithms to perform a mathematical analysis which produces a diagnosis of emotional state and the results are sent to and stored in a remote application server.

9. The system according to claim 1 wherein the subject is seated in the seat and the digital camera is installed near to the seat and is capable of performing a scan of the subject's facial expression and recording the scanned images.

10. The system according to claim 9 wherein the application server is configured to store acquired signals from the digital camera.

11. The system according to claim 1 wherein the subject is seated in the seat and a video monitor is installed in front of the seat for obtaining real-time video images of the subject and providing the video images to the display device.

12. The system according to claim 11 wherein a user interface device is provided by the application server, which executes interface commands in a display of the video monitor for the subject to interact with the system.

13. The system according to claim 1 wherein the subject is seated in the seat and the one or more physiological measuring devices are installed near to the seat and are capable of measuring one or more physiological characteristics of the subject.

14. The system according to claim 1 wherein the system is configured so the subject voluntarily starts the face scanning operation.

15. The system according to claim 1 wherein the digital camera acquires signals and sends the signals to a video monitor and to be stored in the application server.

16. The system according to claim 1 wherein if there is no identification and recognition of a human face, then the user interface sends a real-time image of the seat only to appear in the display of the video monitor device with a text message.

17. The system according to claim 1 wherein if there is no identification and recognition of physiological measurements, then a user interface sends a real-time image of the seat only to appear in the display of a video monitor device with a text message.

18. The system according to claim 1 wherein if there is an identification and recognition of a human face then the user interface device provides a real-time image of the subject in the video display monitor with a text message and then performs the process of diagnosing the subject's emotional state.

19. The system according to claim 1 wherein the results of the analysis of emotional state and obtaining a consensual from the subject is performed through the user interface which is configured to provide a classification of groups of distinct emotional states.

20. The system according to claim 1, wherein communication between the hardware processor and other systems is performed by wire or by wireless signal via Wi-Fi network or via equivalent wireless communications.

21. A passenger seat arrangement including a system for providing noninvasive mental state diagnostics and brain stimulation via transcranial stimulation of a human subject, the passenger seat arrangement comprising:
- a passenger seat including a headrest;
- a digital camera configured for scanning and providing an image of the subject's facial expression while the subject occupies the passenger seat;
- one or more physiological measuring devices comprising one or more transducers, sensors or actuators adapted to measure a physiological parameter of the subject while the subject occupies the passenger seat;
- a seat back comprising a user interface device having a display and an input device for inputting a command or response provided by the subject occupying the passenger seat;
- a processor in communication with the digital camera, the one or more physiological measuring devices, the user interface device, and one or more transducers, sensors or actuators in the head rest, the processor configured to analyze facial expression images obtained by the camera, perform emotional status identification based on the facial expression images and the measured physiological parameter, and operate the user interface device in response to the emotional status identification; and
- the one or more transducers disposed in the head rest and operatively coupled to the processor, the one or more transducers configured to perform transcranial stimulation of the subject based on the emotional status identification while the subject occupies the passenger seat.

* * * * *